United States Patent [19]  
King

[11]  4,428,933  
[45]  Jan. 31, 1984

[54] COMPOSITION FOR TREATING ACNE, METHOD OF MANUFACTURING SAID COMPOSITION, AND METHOD OF TREATING SKIN

[76] Inventor: John R. King, 8414 Greenham Dr., San Antonio, Tex. 78239

[21] Appl. No.: 404,545

[22] Filed: Aug. 2, 1982

[51] Int. Cl.³ .................. A61K 31/075; A61K 31/315; A61K 37/00
[52] U.S. Cl. .......................................... 424/93; 424/95; 424/130; 424/148; 424/165; 424/195; 424/289; 424/338
[58] Field of Search ............... 424/130, 148, 289, 165, 424/338, 195, 93

[56] References Cited

U.S. PATENT DOCUMENTS

| | | | |
|---|---|---|---|
| 411,657 | 9/1889 | Grosbety | 424/145 |
| 2,304,098 | 12/1942 | Jones et al. | 23/147 |
| 3,164,523 | 1/1965 | Fox et al. | 424/365 |
| 4,104,995 | 3/1977 | Juliano et al. | 424/168 |
| 4,255,418 | 3/1981 | Bailey | 424/145 |

*Primary Examiner*—Leonard Shenkman
*Attorney, Agent, or Firm*—Gunn, Lee & Jackson

[57] ABSTRACT

A composition for treating acne, a method of manufacturing same, and a method for treating human skin with said composition. The composition includes specific quantities of pulverized raw oats, sublimed sulfur powder, zinc gluconate, ground whole mustard seed, boric acid powder, brewer's yeast, hydrogen peroxide, isopropyl alcohol, distilled water, methyl p. hydroxybenzoate, and egg yolks.

14 Claims, No Drawings

COMPOSITION FOR TREATING ACNE, METHOD OF MANUFACTURING SAID COMPOSITION, AND METHOD OF TREATING SKIN

BACKGROUND OF THE INVENTION

The presence of acne papules and pustules on human skin is a constant problem faced by those most concerned about their appearance and physical attractiveness. Various types of treatments, medicines, and compositions have been developed in response to this problem. These treatments and compositions have proven to be effective in varying degrees.

The present invention is a new and useful composition and method of manufacturing and using same that has been found to be effective for topical treatment of acne. The composition comprises oats, sulfur, zinc gluconate, mustard seed, boric acid, yeast, a peroxide compound, alcohol, fluid means, a preservative and egg yolks.

The method of manufacturing the above composition comprises grinding oats and mustard seeds to flour consistency and mixing therewith the remaining components listed hereinabove. The ingredients are blended in a conventional fashion for a length of time sufficient to impart a creamy texture to the composition. The method of using the above composition comprises applying a generous amount of the composition to the area to be treated. The composition is allowed to dry and then removed with a damp cloth.

BRIEF DESCRIPTION OF THE PRIOR ART

Various types of treatments, medicines, and compositions have been developed in an effort to treat and control human acne. None, however, disclose the particular ingredients or provide the unique benefits of the present invention.

U.S. Pat. No. 2,304,098 issued to Jones and Notman discloses that zinc compounds and hydrogen peroxide in certain reactive combinations are effective for treating diseases of the skin. However, Jones and Notman also disclose the use of copper or manganese, neither of which are required in the present invention. U.S. Pat. No. 3,164,523 issued to Fox, et al. discloses the use of sulfur and oil of mustard in a gel composition to be used in connection with various cosmetic and medicinal treating agents. However, Fox focuses upon the "gel" quality of his composition and does not disclose the particular ingredients of the present invention. U.S. Pat. No. 4,255,418 and U.S. Pat. No. 411,657 disclose an anti-acne lotion and composition for treating skin diseases, respectively. However, the respective ingredients of the aforementioned patents are different from those of the present invention.

SUMMARY OF THE INVENTION

It is a primary object of the present invention to provide a new and useful composition for effectively treating acne papules and pustules on human skin. The composition includes between about 75% wt and 95% wt of pulverized oats, between about 3.5% wt and 5.5% wt of sulfur, between about 0.001% wt and 0.015% wt of zinc gluconate, between about 0.5% wt and 2.5% wt of mustard seed, between about 2.0% wt and 4.0% wt of boric acid, between about 0.001% wt and 0.009% wt of yeast, between about 0.05% wt and 0.15% wt of a peroxide compound, between about 0.05% wt and 0.15% wt of alcohol, between about 1.5% wt and 3.5% wt of fluid means for imparting a slurry texture to said composition, between about 0.001% wt and 0.009% wt of preservative, and between about 0.05% wt and 0.15% wt of egg yolks. The effectiveness of the above composition has been confirmed in doctor supervised testing.

Another object of the present invention is to provide a method whereby the above composition can be readily manufactured. The method comprises grinding a predetermined amount of raw oats and whole mustard seeds to flour consistency and mixing therewith a predetermined amount of the remaining components listed hereinabove. The ingredients are then blended in a conventional fashion for a length of time sufficient to impart a creamy texture to the composition.

Still another object of the present invention is to provide a method of using the above composition for effectively treating acne. The method comprises applying the above composition to the affected area of the skin, allowing the composition to dry, and then removing the composition from the skin.

A further object of the present invention is to provide a composition for treating acne that is effective as a bactericide against certain bacteria, yeast, and mold. The above composition has been subjected to in vitro testing for initial and long range effectiveness against *Staphylococcus aureus, Escherichia coli, Candida albicans,* and *Aspergillus niger.* The results of these tests indicate that the above composition is an effective bactericide against all of the challenge microorganisms.

A still further object of the present invention is to provide a composition for treating acne that does not cause irritation of the eyes. The above composition was subjected to in vivo testing and proved to cause no deleterious reaction, corneal or conjunctival damage or discharge in any test animal.

Further objects still will be apparent as the invention composition for treating acne and method of manufacturing and using same is described in greater detail hereinbelow.

DETAILED DESCRIPTION OF THE INVENTION

The invention composition for treating acne comprises between about 75% wt and 95% wt of oats, between about 3.5% wt and 5.5% wt of sulfur, between about 0.001% wt and 0.015% wt of zinc gluconate, and between about 0.5% wt and 2.5% wt of mustard seed. The oats are preferably pulverized raw oats, and the sulfur is preferably sublimed sulfur powder. Likewise, the mustard seeds are preferably ground, whole mustard seeds. The composition also includes between about 2.0% wt and 4.0% wt of boric acid, between about 0.001% wt and 0.009% wt of yeast, between about 0.05% wt and 0.15% wt of a peroxide compound, and between about 0.05% wt and 0.15% wt of alcohol. The boric acid is preferably in powder form, and the yeast is preferably brewer's yeast. The peroxide compound is perferably hydrogen peroxide or benzoyl peroxide, and the alcohol is preferably isopropyl alcohol. The composition for treating acne further comprises between about 1.5% wt and 3.5% wt of fluid means, between about 0.001% wt and 0.009% wt of preservative, and between about 0.05% wt and 0.15% wt of egg yolks. The fluid means is used to impart a slurry texture to the composition and is preferably water or distilled water. The preservative is preferably methyl p. hydroxybenzoate.

Within the scope of these limitations, the following percentages and ingredients have been found to be most effective: 88.38% by weight of pulverized raw oats, 4.5% by weight of sublimed sulfur powder, 0.009% by weight of zinc gluconate, 1.5% by weight of ground whole mustard seed, 3.0% by weight of boric acid powder, 0.005% by weight of brewer's yeast, 0.1% by weight of hydrogen peroxide, 0.1% by weight of isopropyl alcohol, 2.3% by weight of distilled water, 0.006% by weight of methyl p. hydroxybenzoate, and 0.1% by weight of egg yolks. Whereas these percentages have yielded the best results, it is to be understood that minor variations in the particular percentages will also produce a composition that is effective for treating acne. In the preferred quantity of approximately 24 ounces, the above composition comprises 16.0 ounces of pulverized raw oats, 0.81 ounces of sublimed sulfur powder, 0.0016 ounces of zinc gluconate, 0.27 ounces of ground whole mustard seed, 0.54 ounces of boric acid powder, 0.0006 ounces of brewer's yeast, 16.0 ml of hydrogen peroxide, 15.0 ml of isopropyl alcohol, 355.0 ml of distilled water, 1.0 ml of methyl p. hydroxybenzoate, and 14.5 ml of egg yolks. Minor variations in the particular quantity of each ingredient will also produce a composition that is effective for treating acne.

The invention acne treatment composition has been subjected to doctor supervised testing and has been shown to be effective for treating human acne. One test involved approximately twenty-four people over a period of several months; six individuals had one follow-up visit and six had ongoing serial evaluations and refills. One of the patients was also using a systemic antibiotic and tretinoin cream and several of the female patients were birth control users. Severity of the acne varied from non-inflammatory comedones (blackheads) to inflammatory papules and pustules.

Overall, the above composition performed as an anti-inflammation and anti-infection treatment against the acne inflammations and eruptions. The pustules healed well and the papules decreased in size and number. The patient's skin became less oily and the presence and new formation of comedones decreased. Depending upon compliancy, the test results indicated a resolution of acne in the range of 75–100%.

Another test involved twenty-five patients over an eight week period. Most of the patients completed the trial period and expressed a decrease in skin irritation and pain. Objectively, the patients exhibited less swelling and redness, as well as fewer and smaller pustules. Those patients with more severe acne exhibited greatest improvement.

The invention composition for treating acne has also been subjected to in vitro and in vivo testing for bacterial kill effectiveness, preservative effectiveness, and propensity to eye irritation. The bacterial kill test involved inoculations of 9 ml of the diluted composition (1:1 with sterile water) with 1 ml of separate inoculum suspensions of *Staphylococcus aureus, Escherichia coli, Candida albicans,* and *Aspergillus niger.* At one minute and three minutes after inoculation, 1.0 ml of the inoculated sample was transferred to 9.0 ml of letheen broth and mixed therewith. From further dilutions in phosphate buffer solution (PBS), pour plates containing 1.0 ml of the inoculated samples were made with letheen agar and incubated at 35° C. for 48 hours.

Each inoculum suspension contained approximately 1,000,000 colony forming units (Cfu) per milliliter and the number of bacteria inoculated into the composition was verified by inoculating 9.0 ml of letheen broth with 1.0 ml of each of the suspensions followed by a similar dilution and incubation procedure. The colony counts made after the incubation period yielded the following results:

| Organisms | Inoculum Level (Cfu/g) | Cfu/g after 1 min. exposure | % Kill | Cfu/g after 3 min. exposure | % Kill |
|---|---|---|---|---|---|
| S. aureus | $150 \times 10^6$ | $65 \times 10^6$ | 57% | $31.1 \times 10^6$ | 79% |
| E. Coli | $41 \times 10^6$ | $15.4 \times 10^6$ | 62% | $10.3 \times 10^6$ | 75% |
| C. Albicans | $32 \times 10^6$ | $6.2 \times 10^6$ | 81% | $2.34 \times 10^6$ | 93% |
| A. niger | $7 \times 10^6$ | $2.2 \times 10^6$ | 69% | $0.18 \times 10^6$ | 97% |

The results of this test indicate that the invention composition is initially effective against the pathogenic bacteria, yeast, and mold tested.

The invention composition was also tested in accordance with the USP XIX "Antimicrobial Preservative Effectiveness" procedure as supplemented by the Federal Register (FDA), Friday, Jan. 6, 1978, "OTC Topical Antimicrobial Products". Pursuant to this test, the composition was challenged twice with *Staphylococcus aureus* (coagulase +), *Escherichia coli, Candida albicans,* and *Aspergillus niger,* and yielded the following results:

INITIAL CHALLENGE
Date Started: 10-07-81

| Organisms | Inoculum Level (Cfu/g) | 24 hours | 1 week | 2 weeks | 3 weeks | 4 weeks |
|---|---|---|---|---|---|---|
| S. aureus | $9.0 \times 10^5$ | 99.9% | 70.9% | 99.4% | 99.5% | 99.9% |
| E. coli | $4.1 \times 10^5$ | 74.9% | 30.0% | 90.5% | 99.9% | 99.9% |
| C. albicans | $8.0 \times 10^5$ | 95.5% | 99.9% | 99.9% | 84.5% | 99.9% |
| A. niger | $3.5 \times 10^5$ | 89.7% | 99.9% | 99.9% | 98.1% | 99.9% |

RE-CHALLENGE
Date Started: 10-22-81

| Organisms | Inoculum Level (Cfu/g) | 24 hours | 1 week | 2 weeks | 3 weeks | 4 weeks |
|---|---|---|---|---|---|---|
| S. aureus | $9.8 \times 10^4$ | 81.2% | 98.1% | 99.9% | 99.9% | 99.99% |
| E. coli | $7.0 \times 10^3$ | 54.3% | 98.6% | 99.9% | 99.9% | 99.99% |
| C. albicans | $7.5 \times 10^4$ | 58.0% | 99.5% | 99.9% | 99.9% | 99.99% |
| A. niger | $6.4 \times 10^4$ | 95.3% | 99.2% | 99.9% | 99.9% | 99.99% |

The results of this test indicate that the preservative system in the invention composition is effective against all of the challenge microorganisms.

The acne treatment composition has also been subjected to in vivo testing for potential eye irritation in accordance with the Federal Register, Vol. 43, No. 163, Section 163.81-4 and Section 163.81-5. Results of this test indicated that the invention composition caused no deleterious reaction, corneal or conjunctival damage or discharge in any test animal. These tests results are particularly significant since acne papules and pustules are often most prevalent in the facial area.

The method of manufacturing the invention acne treatment composition comprises grinding between about 75% wt and 95% wt of oats, preferably raw, to flour consistency and blending the resulting oat flour with between about 3.5% wt and 5.5% wt of sulfur in a conventional mixer. The sulfur ingredient is preferably sublimed sulfur powder. Thereafter, between about 2.0% wt and 4.0% wt of boric acid, preferably in powder form, is added to the mixture and between about 0.5% wt and 2.5% wt of mustard seeds are ground to flour consistency and added to the aforementioned ingredients. Thereafter, between about 0.001% wt and 0.015% wt of zinc gluconate and between about 0.001% wt and 0.009% wt of yeast are added to the mixture and blended for approximately 30 minutes. The yeast is preferably brewer's yeast. A predetermined amount of each of the following components is then added to the mixture: between about 1.5% wt and 3.5% wt fluid means, between about 0.05% wt and 0.15% wt of a peroxide compound, between about 0.05% wt and 0.15% wt of alcohol, between about 0.001% wt and 0.009% wt of preservative, and between about 0.05% wt and 0.15% wt of egg yolks. The entire composition is then blended approximately 30 minutes or until the mixture achieves a creamy texture. The fluid means is preferably distilled water and the peroxide compound is preferably hydrogen peroxide. Likewise, the alcohol is preferably isopropyl alcohol and the preservative is preferably methyl p. hydroxybenzoate.

Although the method of manufacturing the acne treatment composition has been described in accordance with the preferred embodiment, it is also contemplated that the above described ingredients can be combined in any particular order and blended to the consistency and texture desired. For example, the oats and mustard seeds can be ground together and subsequently combined with a previously mixed solution of the remaining ingredients prior to blending. The particular percentage of each ingredient may also be varied somewhat without departing from the effectiveness of the composition.

The method of using the invention composition comprises topical application of the composition to the area of skin to be treated. It is to be understood tht the area to be treated is clean and dry and that the actual amount of composition applied can be varied as needed. Once the composition has been applied to the skin, it is allowed to dry and then removed with a damp cloth.

While the invention acne treatment composition and method of manufacturing and using same has been described in connection with the preferred embodiment, it is not intended to limit the invention to the particular form set forth, but on the contrary, is intended to cover such alternatives, modifications, and equivalents as may be included within the spirit and scope of the invention as defined by the appended claims.

I claim:

1. A composition for treating acne comprising: between about 75% wt and 95% wt of pulverized oats, between about 3.5% wt and 5.5% wt of sulfur, between about 0.001% wt and 0.015% wt of zinc gluconate, between about 0.5% wt and 2.5% wt of mustard seed, between about 2.0% wt and 4.0% wt of boric acid, between about 0.001% wt and 0.009% wt of yeast, between about 0.05% wt and 0.15% wt of a peroxide compound, between about 0.05% wt and 0.15% wt of alcohol, between about 1.5% wt and 3.5% wt of an additional fluid, and between about 0.05% wt and 0.15% wt of egg yolks.

2. A composition for treating acne, as recited in claim 1, wherein said additional fluid is distilled water.

3. A composition for treating acne, as recited in claim 1, wherein said peroxide compound is hydrogen peroxide.

4. A composition for treating acne, as recited in claim 1, wherein said peroxide compound is benzoyl peroxide.

5. A composition for treating acne, as recited in claim 1, additionally containing between about 0.001% wt and 0.009% wt of preservative.

6. A composition for treating acne in the form of a creamy textured substance, comprising: approximately 88.38% by weight of pulverized oats, approximately 4.5% by weight of sulfur, approximately 0.009% by weight of zinc gluconate, approximately 1.5% by weight of mustard seed, approximately 3.0% by weight of boric acid, approximately 0.005% by weight of yeast, approximately 0.1% by weight of a peroxide compound, approximately 0.1% by weight of alcohol, approximately 2.3% by weight of water, approximately 0.006% by weight of preservative, and approximately 0.1% by weight of egg yolks.

7. A composition for treating acne, comprising: approximately 16.0 oz. of pulverized raw oats, approximately 0.81 oz. of sublimed sulfur powder, approximately 0.0016 oz. of zinc gluconate, approximately 0.27 oz. of ground whole mustard seed, approximately 0.54 oz. of boric acid powder, approximately 0.0006 oz. of brewer's yeast, approximately 16.0 ml of hydrogen peroxide, approximately 15.0 ml of isopropyl alcohol, approximately 355.0 ml of water, approximately 1.0 ml of methyl p. hydroxybenzoate, and approximately 14.5 ml of egg yolks.

8. A composition for treating acne, as recited in claim 6 or 7, wherein said water is distilled.

9. A method of manufacturing a composition for treating acne comprising the steps of:
   (a) grinding between about 75% wt and 95% wt of oats and between about 0.5% wt and 2.5% wt of mustard seeds to flour consistency;
   (b) mixing between about 3.5% wt and 5.5% wt of sulfur, between about 0.001% wt and 0.015% wt of zinc gluconate, between about 2.0% wt and 4.0% wt of boric acid, between about 0.001% wt and 0.009% wt of yeast, between about 0.05% wt and 0.15% wt of a peroxide compound, between about 0.05% wt and 0.15% wt of alcohol, between about 1.5% wt and 3.5% wt of an additional fluid, and between about 0.05% wt and 0.15% wt of egg yolks;
   (c) combining said mixture of step (b) with said mixture of step (a); and
   (d) blending the composition of step (c).

10. A method of manufacturing a composition for treating acne, comprising the steps of:
   (a) grinding between about 75% wt and 95% wt of raw oats to flour consistency;
   (b) adding between about 3.5% wt and 5.5% wt of sublimed sulfur powder to said raw oats of step (a);
   (c) adding between about 2.0% wt and 4.0% wt boric acid powder to the mixture of step (b);
   (d) grinding between about 0.5% wt and 2.5% wt of whole mustard seed to flour consistency;
   (e) adding said ground mustard seed of step (d) to the mixture of step (c);
   (f) adding between about 0.001% wt and 0.015% wt of zinc gluconate and between about 0.001% wt and 0.009% wt of brewer's yeast to the mixture of step (e);
   (g) blending the composition of step (f);
   (h) adding between about 1.5% wt and 3.5% wt of distilled water, between about 0.05% wt and 0.15% wt of hydrogen peroxide, between about 0.05% wt and 0.15% wt of isopropyl alcohol, between about 0.001% wt and 0.009% wt of methyl p. hydroxybenzoate, and between about 0.05% wt and 0.15% wt of egg yolks, to the mixture of step (g);

(i) blending the composition of step (h) until said composition achieves a creamy texture.

11. A composition for treating acne prepared by the method of claim 9.

12. A method of treating skin, comprising the steps of:
(a) applying to the skin an effective amount of the composition of claim 1 or 11;
(b) allowing said composition to dry; and
(c) removing said composition from said skin.

13. A composition for treating acne, comprising: between about 75% wt and 95% wt of pulverized oats, between about 3.5% wt and 5.5% wt of sulfur, between about 0.001% wt and 0.015% wt of zinc gluconate, between about 0.5% wt and 2.5% wt of mustard seed, between about 2.0% wt and 4.0% wt of boric acid, between about 0.001% wt and 0.009% wt of yeast, between about 0.05% wt and 0.15% wt of a peroxide compound, between about 0.05% wt and 0.15% wt of alcohol, between about 1.5% wt and 3.5% wt of water for imparting a slurry texture to said composition, between about 0.001% wt and 0.009% wt of preservative, and between about 0.05% wt and 0.15% wt of egg yolks.

14. A method of manufacturing a composition for treating acne, comprising the steps of:
(a) grinding between about 75% wt and 95% wt of oats and between about 0.5% wt and 2.5% wt of mustard seeds to flour consistency;
(b) mixing between about 3.5% wt and 5.5% wt of sulfur, between about 0.001% wt and 0.015% wt of zinc gluconate, between about 2.0% wt and 4.0% wt of boric acid, between about 0.001% wt and 0.009% wt of yeast, between about 0.05% wt and 0.15% wt of a peroxide compound, between about 0.05% wt and 0.15% wt of alcohol, between about 1.5% wt and 3.5% wt of water, between about 0.001% wt and 0.009% wt of preservative, and between about 0.05% wt and 0.15% wt of egg yolks;
(c) combining said mixture of step (b) with said mixture of step (a); and
(d) blending the composition of step (c).

* * * * *